(12) United States Patent
Rey et al.

(10) Patent No.: US 6,730,346 B2
(45) Date of Patent: May 4, 2004

(54) METHODS FOR USING LIPASES IN BAKING

(75) Inventors: Michael W. Rey, Davis, CA (US); Elizabeth J. Golightly, Davis, CA (US); Tina Spendler, Hjortespringparken 40 (DK)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 10/429,398

(22) Filed: May 5, 2003

(65) Prior Publication Data

US 2003/0180418 A1 Sep. 25, 2003

Related U.S. Application Data

(62) Division of application No. 09/703,414, filed on Oct. 31, 2000, now Pat. No. 6,558,715.

(51) Int. Cl.[7] .............................. A21D 10/00; A21D 2/08
(52) U.S. Cl. ........................................ 426/555; 426/653
(58) Field of Search ............................ 426/20, 52, 549, 426/653, 555; 435/198

(56) References Cited

U.S. PATENT DOCUMENTS 6,309,869 B1 * 10/2001 Yaver et al. ................. 435/196

FOREIGN PATENT DOCUMENTS

| EP | 0869167 | | 12/1997 |
| WO | 97/26330 | * | 7/1997 |
| WO | WO 98/26057 | | 6/1998 |

* cited by examiner

Primary Examiner—Keith Hendricks
(74) Attorney, Agent, or Firm—Robert L. Stamos

(57) ABSTRACT

The present invention relates to methods for preparing a dough, comprising incorporating into the dough a composition comprising an effective amount of a lipase which improves one or more properties of the dough or a baked product obtained from the dough. The present invention also relates to methods for preparing a baked product. The present invention also relates to compositions comprising an effective amount of such a lipase for improving one or more properties of a dough and/or a baked product obtained from the dough. The present invention further relates to doughs or baked products and to pre-mixes for a dough.

20 Claims, 8 Drawing Sheets

Fig. 1A

```
GCAAGGCGAACCCTTCGTTCAAGGTCGTTGCCACAGGTCACTCGTTGGGGTGGTGCTGTAGCTACACTAGC   2030
 R  K  A  N  P  S  F  K  V  V  A  T  G  H  S  L  G  G  A  V  A  T  L  A
AGGTGCGAACCTGCGAGTTGGTGGTACGCCAGTTGACATCTACACCTACGGCTCACCCCGAGTTGGAAAC   2100
 G  A  N  L  R  V  G  G  T  P  V  D  I  Y  T  Y  G  S  P  R  V  G  N
ACGCAACTCGCTGCCTTCATCTCTAACCAGGCTGGTGGAGAGTTCGCGTTACGAACGCCAAGGACCCCG   2170
 T  Q  L  A  A  F  I  S  N  Q  A  G  G  E  F  R  V  T  N  A  K  D  P
TGCCTCGTCTCCCCCCTCTGGTCTTTGGATACCGGGCACACATCCCCGAGTACTGGTTGTCTGGTAGCGG   2240
 V  P  R  L  P  P  L  V  P  G  Y  R  H  T  S  P  E  Y  W  L  S  G  S  G
AGGTAACAAGGTTGACTACACCATCAATGATGTCAAGGTGTGTGAGGGTGCGCAACCTTCAGTGCAAC   2310
 G  N  K  V  D  Y  T  I  N  D  V  K  V  C  E  G  A  A  N  L  Q  C  N
GGTGGAACACTCGGATTGGAGATATCGACGCCCATCTCCACTCTTCCAGGAGACCGATGCTTGCTCTGGTT   2380
 G  G  T  L  G  L  D  I  D  A  H  L  H  Y  F  Q  E  T  D  A  C  S  G
CCGGTATCGCGTGGAGAAGATACAGAGGAGTGCTAAGCGTGAGAGCATCTCGGAGAGGGCCACTATGACAGA   2450
 S  G  I  A  W  R  R  Y  R  S  A  K  R  E  S  I  S  E  R  A  T  M  T  D
TGCCGAGCTGGAGAAGAAGCTTAACAACTATGTTGCGATGGATAAGGAGTATGTCAAGACTCACGCCAAC   2520
 A  E  L  E  K  K  L  N  N  Y  V  A  M  D  K  E  Y  V  K  T  H  A  N
CGCTCATCATCGTAGTATGACATTTACGCAGTAACGATATAATTACCAGTAATGTATCATAACCTGGATACCATTCT   2590
 R  S  S
GGTGCAAGCATGGCGAAGAAACATCATTATCTATGTGAATGTATCATAACCTCCTTACGCCATGCCGT   2660
TGATCTTACTACTGAGACAACAAAATACTCAGTCATGTACAACAAACTCCAAAGCACCGAATGACTTCTGGCT   2730
TTTTGGCAAAGCACACCGAGAAACGAGAAACCAATCATTCAAACCCCTCCACCTTCATGCCCTGCGCATTGGAACACCCAC   2800
GAGAATGACACCACGAGGCACGCACGCGAAACCCCAAAGAGACATTGACTTCCCGGATA   2870
TTAGGGCATGCTCGGAAATGAACCCAGAGAACAAATCCGTCACTGCCTCACAGAAACTGATCTCCAATT   2940
```

Fig. 1B

SEQUENCE LISTING

<160> NUMBER OF SEQ ID NOS: 10

<210> SEQ ID NO 1
<211> LENGTH: 2940
<212> TYPE: DNA
<213> ORGANISM: Fusarium venenatum

<400> SEQUENCE: 1

```
aattcatgtg aatctactat gtaacagtat gttgtattgc attacccatc aacgttgaat      60
cgttgcgacg taacggcccg gttcaagcga gatgtagata tgttggtagt taattgatgg     120
gttaggtatt cttttcatca actcggtatt ctcattcccc agatatcggc acttgtcttt     180
actccagatt tcatatcgca tcgagttata tacagtccca attgagtcga ctaccccgtc     240
caaaacaggt tttctcacaa accaaccgca gcctaacaaa aagtcccttg tctttctgca     300
ataaatgctg acaccccctg cttttagg actgacggct cacgatgcag ccgttgcgat       360
aattaattga caattacccg cacattgatg catacttggc ggtcaggtca ggtcaggctg     420
aagcatacct attgggtcat ttatttgccg atcgtggtga aaagaatgca agtgataact     480
agttacgagt cgctttatga aagatggttg gtcgaaactg tcaatatggc atgggcggca    540
aatcgtttgg tctcaactct atagcatgta ctataattgg tcttttcatc acagtcacgc     600
caaagtgcca gtctcagact atggaccaac cactttcctc cttcacgtct aaattgactt     660
gatcaccaga ctcgaatatt ttttcttttc ttctataccc ctaggatcat acaatacgaa     720
ccccaactca actcgagaga gagagtcccc ttcccaacat tttgacagcc cttgctcttc     780
tcctcccagg atgtaacaga agctgaaagg gtacccctgt agcccacctt tacccaccat    840
cttttccatc tgtatcggtg catcccatca caaccctcac gtggtccgag atcgtcgtta     900
cccgtattgg aagctcactc cgggcccaac gagagattgg accaaggaaa ataactttg      960
agacctcttc aagcagtcgg tcattcgtta ctgggatgtg tagtcgataa tgcggggtga   1020
caggccctca atccagcacc caccatcatg ggcactgact gtactaccgg agcccatcat   1080
ttcgtttttg ggtcctggcg tctacttgac cgactgagtt tgccaagatg gatggcatga   1140
gagacagtgg ttaggctggg cgggtattgt gatgagagaa agcgagagac tagttagaag   1200
caaagaaaaa agatatataa gctgtcacat ccctcatgaa catgctgttc ttgtaagtcg   1260
ggatatcagg gccagcttca gtattcagta tcctttctga gggagttgca ccttgtcaca   1320
gcttgtctgt ctatcactta tacttaccct tggaccacgt tctttgtctg tcaagatgca   1380
tctcctatca ctcctctcaa ttgccaccct tgcggtagcc agccctctga gcgttgaaga   1440
ttacgccaag gctctcgatg aaagaggtaa aacgattctc tgttcccata acaattccaa   1500
tactcacaga cctagctgtt tctgtctcta ccaacgactt tggcaacttc aagttctaca   1560
tccagcacgg tgccgcagca tactgtaact ctgaagccgc agccggtgca aaggtcacct   1620
gcggaggaaa cggttgccca acggtccagt ccaatggtgc caccatcgtg gcatcttttcc  1680
tgtaagtcta acatatcaca aacacatcat caactccaaa cttacaaatc tctttatagt   1740
ggctcaaaga ctggcatcgg tggctacgtc gcgaccgact ctgcacgcaa ggaaatcgtc   1800
ctctcggttc gcggtagcac caacattcgc aactggctta ccaacctcga cttcgaccag   1860
gatgactgca gcttgacctc cggctgtgga gtgcacggag gcttccagag agcctggaat   1920
gagatctcgg ccgcagcaac cgccgctgtc gcaaaggccc gcaaggcgaa cccttcgttc   1980
aaggtcgttg ccacaggtca ctcgttgggt ggtgctgtag ctacactagc aggtgcgaac   2040
```

-continued

```
ctgcgagttg gtggtacgcc agttgacatc tacacctacg gctcacccg agttggaaac    2100
acgcaactcg ctgccttcat ctctaaccag gctggtggag agttccgcgt tacgaacgcc    2160
aaggaccccg tgcctcgtct cccccctctg gtctttggat accggcacac atcccccgag    2220
tactggttgt ctggtagcgg aggtaacaag gttgactaca ccatcaatga tgtcaaggtg    2280
tgtgagggtg ctgccaacct tcagtgcaac ggtggaacac tcggattgga tatcgacgcc    2340
catctccact acttccagga gaccgatgct tgctctggtt ccggtatcgc gtggagaaga    2400
tacaggagtg ctaagcgtga gagcatctcg gagagggcca ctatgacaga tgccgagctg    2460
gagaagaagc ttaacaacta tgttgcgatg gataaggagt atgtcaagac tcacgccaac    2520
cgctcatcgt agtatgacat ttacgcagta acgatataat taccataaca aaaactctgg    2580
ataccattct ggtgcaagca tggcgaagaa acatcatta tctatgtgaa tgtatcataa    2640
ccatccttac gccatgccgt tgatcttact actgagacaa aatactcagt catgtacaac    2700
aaactccaaa gcaccgaatg acttctggct ttttggcaaa gcacgaaacc aatcattcaa    2760
accccctccac gaccatgccc tgcgcattgg gaacacccac gagaatgaca ccacgaggca    2820
cgcggacact cttcaccttc atgcacccaa agacattgac ttcccggata ttagggcatg    2880
ctcggaaaat ggaacccaga acaaaatccg tcactgcctc acagaaactg atctccaatt    2940
```

<210> SEQ ID NO 2
<211> LENGTH: 349
<212> TYPE: PRT
<213> ORGANISM: Fusarium venenatum

<400> SEQUENCE: 2

```
Met His Leu Leu Ser Leu Leu Ser Ile Ala Thr Leu Ala Val Ala Ser
1               5                   10                  15

Pro Leu Ser Val Glu Asp Tyr Ala Lys Ala Leu Asp Glu Arg Ala Val
            20                  25                  30

Ser Val Ser Thr Asn Asp Phe Gly Asn Phe Lys Phe Tyr Ile Gln His
        35                  40                  45

Gly Ala Ala Tyr Cys Asn Ser Glu Ala Ala Gly Ala Lys Val
    50                  55                  60

Thr Cys Gly Gly Asn Gly Cys Pro Thr Val Gln Ser Asn Gly Ala Thr
65                  70                  75                  80

Ile Val Ala Ser Phe Leu Gly Ser Lys Thr Gly Ile Gly Gly Tyr Val
                85                  90                  95

Ala Thr Asp Ser Ala Arg Lys Glu Ile Val Leu Ser Val Arg Gly Ser
            100                 105                 110

Thr Asn Ile Arg Asn Trp Leu Thr Asn Leu Asp Phe Asp Gln Asp Asp
        115                 120                 125

Cys Ser Leu Thr Ser Gly Cys Gly Val His Gly Phe Gln Arg Ala
    130                 135                 140

Trp Asn Glu Ile Ser Ala Ala Ala Thr Ala Ala Val Ala Lys Ala Arg
145                 150                 155                 160

Lys Ala Asn Pro Ser Phe Lys Val Val Ala Thr Gly His Ser Leu Gly
                165                 170                 175

Gly Ala Val Ala Thr Leu Ala Gly Ala Asn Leu Arg Val Gly Gly Thr
            180                 185                 190

Pro Val Asp Ile Tyr Thr Tyr Gly Ser Pro Arg Val Gly Asn Thr Gln
        195                 200                 205

Leu Ala Ala Phe Ile Ser Asn Gln Ala Gly Gly Glu Phe Arg Val Thr
```

```
            210                 215                 220
Asn Ala Lys Asp Pro Val Pro Arg Leu Pro Pro Leu Val Phe Gly Tyr
225                 230                 235                 240

Arg His Thr Ser Pro Glu Tyr Trp Leu Ser Gly Ser Gly Gly Asn Lys
                245                 250                 255

Val Asp Tyr Thr Ile Asn Asp Val Lys Val Cys Glu Gly Ala Ala Asn
            260                 265                 270

Leu Gln Cys Asn Gly Gly Thr Leu Gly Leu Asp Ile Asp Ala His Leu
        275                 280                 285

His Tyr Phe Gln Glu Thr Asp Ala Cys Ser Gly Ser Gly Ile Ala Trp
    290                 295                 300

Arg Arg Tyr Arg Ser Ala Lys Arg Glu Ser Ile Ser Glu Arg Ala Thr
305                 310                 315                 320

Met Thr Asp Ala Glu Leu Glu Lys Lys Leu Asn Asn Tyr Val Ala Met
                325                 330                 335

Asp Lys Glu Tyr Val Lys Thr His Ala Asn Arg Ser Ser
            340                 345

<210> SEQ ID NO 3
<211> LENGTH: 35
<212> TYPE: DNA
<213> ORGANISM: Fusarium venenatum

<400> SEQUENCE: 3
cagtgaattg gcctcgatgg ccgcggccgc gaatt                           35

<210> SEQ ID NO 4
<211> LENGTH: 35
<212> TYPE: DNA
<213> ORGANISM: Fusarium venenatum

<400> SEQUENCE: 4
aattcgcggc cgcggccatc gaggccaatt cactg                           35

<210> SEQ ID NO 5
<211> LENGTH: 34
<212> TYPE: DNA
<213> ORGANISM: Fusarium venenatum

<400> SEQUENCE: 5
cacgaaggaa agacgatggc tttcacggtg tctg                            34

<210> SEQ ID NO 6
<211> LENGTH: 34
<212> TYPE: DNA
<213> ORGANISM: Fusarium venenatum

<400> SEQUENCE: 6
cagacaccgt gaaagccatc gtctttcctt cgtg                            34

<210> SEQ ID NO 7
<211> LENGTH: 46
<212> TYPE: DNA
<213> ORGANISM: Fusarium venenatum

<400> SEQUENCE: 7
ctatctcttc accatggtac cttaattaaa taccttgttg gaagcg               46

<210> SEQ ID NO 8
<211> LENGTH: 46
```

```
-continued

<212> TYPE: DNA
<213> ORGANISM: Fusarium venenatum

<400> SEQUENCE: 8
cgcttccaac aaggtattta attaaggtac catggtgaag agatag                46

<210> SEQ ID NO 9
<211> LENGTH: 37
<212> TYPE: DNA
<213> ORGANISM: Fusarium venenatum

<400> SEQUENCE: 9
cgttctttgt ctgtcagcat gcatctccta tcactcc                          37

<210> SEQ ID NO 10
<211> LENGTH: 45
<212> TYPE: DNA
<213> ORGANISM: Fusarium venenatum

<400> SEQUENCE: 10
ccagagtttt tgttatggtt aattaatatc gttactgcgt aaatg                 45
```

METHODS FOR USING LIPASES IN BAKING

This application is a divisional application of U.S. application Ser. No. 09/703,414, filed Oct. 31, 2000, now U.S. Pat. No. 6,558,715, the contents of which are fully incorporated herein by reference.

BACKGROUND OF THE INVENTION

1. Field of the Invention

The present invention relates to methods for preparing a dough and/or baked product with a lipase.

2. Description of the Related Art

The strength of a dough is an important aspect of baking for both small-scale and large-scale applications. A strong dough has a greater tolerance of mixing time, proofing time, and mechanical vibrations during dough transport, whereas a weak dough is less tolerant to these treatments. A strong dough with superior rheological and handling properties results from flour containing a strong gluten network. Flour with a low protein content or a poor gluten quality results in a weak dough.

Dough "conditioners" are well known in the baking industry. The addition of conditioners to bread dough has resulted in improved machinability of the dough and improved texture, volume, flavor, and freshness (anti-staling) of the bread. Nonspecific oxidants, such as iodates, peroxides, ascorbic acid, potassium bromate and azodicarbonamide have a gluten strengthening effect. It has been suggested that these conditioners induce the formation of interprotein bonds which strengthen the gluten, and thereby the dough. However, the use of several of the currently available chemical oxidizing agents has been met with consumer resistance or is not permitted by regulatory agencies.

The use of enzymes as dough conditioners has been considered as an alternative to chemical conditioners. A number of enzymes have been used recently as dough and/or bread improving agents, in particular, enzymes that act on components present in large amounts in the dough. Examples of such enzymes are amylases, proteases, glucose oxidases, and (hemi)cellulases, including pentosanases.

WO 98/26057 discloses a polypeptide having lipase and phospholipase activity (GenBank Acc. No. A85215) obtained from *Fusarium oxysporum*. The enzyme has a molecular weight of 30±2 kDa, an isoelectric point of 5.8–6.8, and optimum phospholipase activity above pH 9.

It is the object of the present invention to improve the properties of dough and/or baked products by the use of a lipase.

SUMMARY OF THE INVENTION

The present invention relates to methods for preparing a dough, comprising incorporating into the dough an effective amount of a lipase selected from the group consisting of.

(a) a lipase having an amino acid sequence which has at least 85% identity with amino acids 31 to 350 of SEQ ID NO:2;

(b) a lipase encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii) of at least 100 nucleotides, or (iv) a complementary strand of (i), (ii), or (iii); and (c) a variant of the polypeptide having an amino acid sequence of SEQ ID NO:2 comprising a substitution, deletion, and/or insertion of one or more amino acids; and (d) a fragment of (a) or (b), which has lipase activity.

The present invention also relates to methods for preparing a baked product with such a lipase.

The present invention also relates to compositions comprising an effective amount of such a lipase, for improving one or more properties of a dough and/or a baked product obtained from the dough, and a carrier and/or a baking ingredient.

The present invention also relates to dough or baked products.

The present invention further relates to pre-mixes for a dough comprising an effective amount of such a lipase, for improving one or more properties of a dough and/or a baked product obtained from the dough, and a carrier and/or a baking ingredient.

BRIEF DESCRIPTION OF THE FIGURES

FIGS. 1A and 1B show the genomic DNA sequence and the deduced amino acid sequence of a *Fusarium venenatum* lipase (SEQ ID NOS:1 and 2, respectively).

DETAILED DESCRIPTION OF THE INVENTION

Figure 2:
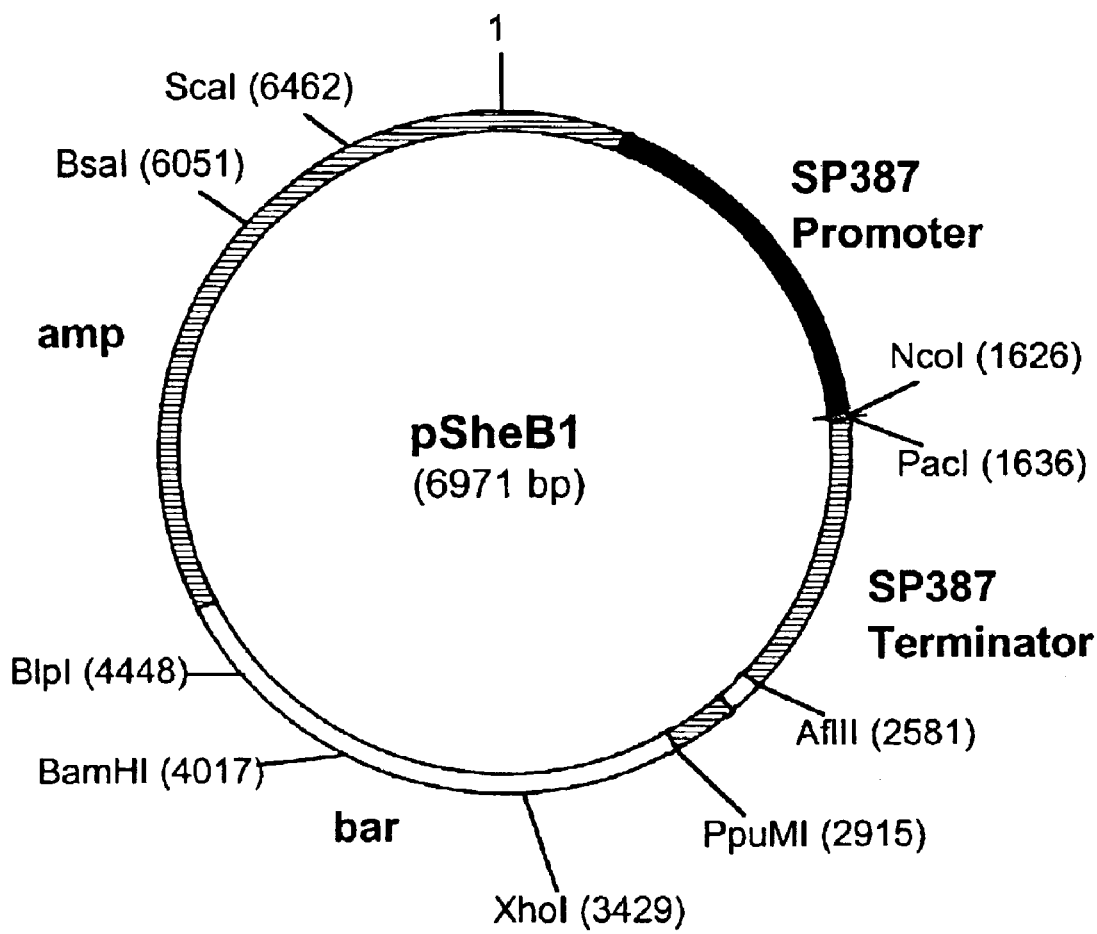
FIG. 2 shows a restriction map of pSheB1.

The present invention relates to methods for preparing a dough or a baked product comprising incorporating into the dough an effective amount of a lipase to improve one or more properties of the dough or the baked product obtained from the dough relative to a dough or a baked product in which a lipase is not incorporated, wherein the lipase is selected from the group consisting of:

(a) a lipase having an amino acid sequence which has at least 85% identity with amino acids 31 to 350 of SEQ ID NO:2;

(b) a lipase encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii) of at least 100 nucleotides, or (iv) a complementary strand of (i), (ii), or (iii); and (c) a variant of the polypeptide having an amino acid sequence of SEQ ID NO:2 comprising a substitution, deletion; and/or insertion of one or more amino acids; and (d) a fragment of (a) or (b), which has lipase activity.

The term "lipase activity" is defined herein as a triacylglycerol acylhydrolase activity which catalyzes the hydrolysis of a triacylglycerol to diacylglycerol and a fatty acid anion.

A substrate for measuring lipase activity is prepared by emulsifying tributyrin (glycerin tributyrate) using gum Arabic as emulsifier. The hydrolysis of tributyrin at 30° C. and pH 7 is followed by a pH-stat titration. One unit of lipase activity (1 LU) equals the amount of enzyme capable of releasing 1 μmol butyric acid/minute at the standard conditions. 1 KLU=1000 LU. Lipase activity may also be determined by measuring the hydrolysis of 2 mM p-nitrophenyl butyrate in 100 mM MOPS pH 7.5, 4 mM $CaCl_2$, 990 μl of DMSO, 80 μl of 1% AOS at pH 7.5, 25° C. One unit of lipase activity is defined as 1.0 μmole of p-nitrophenolate anion produced per minute at 25° C., pH 7.5.

In a first embodiment of the methods of the present invention, the lipase has an amino acid sequence which has a degree of identity to amino acids 31 to 350 of SEQ ID NO:2 (i.e., the mature polypeptide) of at least about 85%, preferably at least about 90%, more preferably at least about 95%, and most preferably at least about 97%, which have lipase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 31 to 350 of SEQ ID NO:2. For purposes of the present invention, the degree of identity between two amino acid sequences is determined by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

Preferably, the lipase in the methods of the present invention comprise the amino acid sequence of SEQ ID NO:2 or an allelic variant thereof; or a fragment thereof that has lipase activity. In a more preferred embodiment, the lipase comprises the amino acid sequence of SEQ ID NO:2. In another preferred embodiment, the lipase comprises amino acids 31 to 350 of SEQ ID NO:2, or an allelic variant thereof; or a fragment thereof that has lipase activity. In another preferred embodiment, the lipase comprises amino acids 31 to 350 of SEQ ID NO:2. In another preferred embodiment, the lipase consists of the amino acid sequence of SEQ ID NO:2 or an allelic variant thereof; or a fragment thereof that has lipase activity. In another preferred embodiment, the lipase consists of the amino acid sequence of SEQ ID NO:2. In another preferred embodiment, the lipase consists of amino acids 31 to 350 of SEQ ID NO:2 or an allelic variant thereof; or a fragment thereof-that has lipase activity. In another preferred embodiment, the lipase consists of amino acids 31 to 350 of SEQ ID NO:2.

A fragment of SEQ ID NO:2 is a polypeptide having one or more amino acids deleted from the amino and/or carboxyl terminus of this amino acid sequence. Preferably, a fragment contains at least 260 amino acid residues, more preferably at least 280 amino acid residues, and most preferably at least 300 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment of the methods of the present invention, the lipases are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 1525 to 2530 of SEQ ID NO:1, (ii) the cDNA sequence contained in nucleotides 1525 to 2530 of SEQ ID NO:1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO:1 may be at least 100 nucleotides or preferably at least 200 nucleotides. Moreover, the subsequence may encode a polypeptide fragment which has lipase activity. The lipases may also be allelic variants or fragments of the lipases.

The nucleic acid sequence of SEQ ID NO:1 or a subsequence thereof, as well as the amino acid sequence of SEQ ID NO:2 or a fragment thereof, may be used to design a nucleic acid probe to identify and clone DNA encoding such lipases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic DNA or cDNA library prepared from such other organisms may be screened for DNA which hybridizes with the probes described above and which encodes such a lipase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO:1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the lipase of SEQ ID NO:2, or a subsequence thereof. In another preferred embodiment, the nucleic acid probe is SEQ ID NO:1. In another preferred embodiment, the nucleic acid probe is the mature lipase coding region of SEQ ID NO:1. In another preferred embodiment, the nucleic acid probe is the nucleic acid sequence contained in plasmid pEJG60 which is contained in *Escherichia coli* NRRL B-30333, wherein the nucleic acid sequence encodes a lipase. In another preferred embodiment, the nucleic acid probe is the mature lipase coding region contained in plasmid pEJG60 which is contained in *Escherichia coli* NRRL B-30333.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, Proceedings of the National Academy of Sciences USA 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third embodiment of the methods of the present invention, the lipase is a variant of the lipase having an amino acid sequence of SEQ ID NO:2 comprising a substitution, deletion, and/or insertion of one or more amino acids.

The amino acid sequence of the variant lipase may differ from the amino acid sequence of SEQ ID NO:2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The lipases of the methods of the present invention have at least 20%, preferably at least 40%, more preferably at least 60%, even more preferably at least 80%, even more preferably at least 90%, and most preferably at least 100% of the lipase activity of the mature polypeptide of SEQ ID NO:2.

The lipase may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted. In a preferred embodiment, the polypeptide is secreted extracellularly.

The lipase may be a bacterial polypeptide. For example, The lipase may be a gram positive bacterial lipase such as a Bacillus lipase, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a Streptomyces lipase, e.g., a *Streptomyces lividans* or *Streptomyces murinus* lipase; or a gram negative bacterial lipase, e.g., an *E. coli* or a Pseudomonas sp. lipase.

The lipase may be a fungal lipase, and more preferably a yeast lipase such as a Candida, Kluyveromyces, Pichia, Saccharomyces, Schizosaccharomyces, or Yarrowia lipase; or more preferably a filamentous fungal lipase such as an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma lipase.

In a preferred embodiment, the lipase is a *Saccharomyces carisbergensis, Saccharomyces cerevisiae, Saccharomyces diastaticus, Saccharomyces douglasii, Saccharomyces kluyveri, Saccharomyces norbensis* or *Saccharomyces oviformis* lipase.

In another preferred embodiment, the lipase is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotnchioides, Fusarium sulphureum, Fusarium torulosum, Fusarium trichothecioides, Fusarium venenatum, Humicola insolens, Humicola lanuginosa, Mucor miehei, Myceliophthora thernophila, Neurospora crassa, Penicillium purpurogenum, Trichoderma harzianum, Trichoderma koningii, Trichoderma longibrachiatum, Trichoderma reesei*, or *Trichoderma viride* lipase.

In another preferred embodiment, the lipase is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* lipase.

In a more preferred embodiment, the *Fusarium venenatum* strain is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium*

*venenatum* regardless of the species name by which they are currently known. In another preferred embodiment, the *Fusarium venenatum* strain is a morphological mutant of *Fusarium venenatum* A3/5 or *Fusarium venenatum* ATCC 20334, as disclosed in WO 97/26330.

It will be understood that for the aforementioned species, both the perfect and imperfect states are encompassed and other taxonomic equivalents, e.g., anamorphs, regardless of the species name by which they are known. Those skilled in the art will readily recognize the identity of appropriate equivalents. For example, taxonomic equivalents of Fusanum are defined by D. L. Hawksworth, P. M. Kirk, B. C. Sutton, and D. N. Pegler (editors), 1995, In Ainsworth & Bisby's *Dictionary of the Fungi*, Eighth Edition, CAB International, University Press, Cambridge, England, pp. 173–174.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such lipases may be identified and obtained from other sources including microorganisms isolated from nature (e.g., soil, composts, water, etc.) using the abovementioned probes. Techniques for isolating microorganisms from natural habitats are well known in the art. The nucleic acid sequence may then be derived by similarly screening a genomic or cDNA library of another microorganism. Once a nucleic acid sequence encoding a lipase has been detected with the probe(s), the sequence may be isolated or cloned by utilizing techniques which are known to those of ordinary skill in the art (see, e.g., Sambrook et al., 1989, supra).

As defined herein, an "solated" lipase is a lipase which is essentially free of other non-lipases, e.g., at least about 20% pure, preferably at least about 40% pure, more preferably about 60% pure, even more preferably about 80% pure, most preferably about 90% pure, and even most preferably about 95% pure, as determined by SDS-PAGE.

The lipase may be obtained from the organism in question by any suitable technique, and in particular by use of recombinant DNA techniques known in the art (c.f. Sambrook, J. et al., 1989, *Molecular Cloning, A Laboratory Manual*, Cold Spring Harbor Press, Cold Spring Harbor, N.Y., USA). The use of recombinant DNA techniques generally comprises cultivation of a host cell transformed with a recombinant DNA vector, consisting of the product gene of interest inserted between an appropriate promoter and terminator, in a culture medium under conditions permitting the expression of the enzyme and recovering the enzyme from the culture. The DNA sequence may be of genomic, cDNA, or synthetic origin, or any mixture of these, and may be isolated or synthesized in accordance with methods known in the art.

The phrase "incorporating into the dough" is defined herein as adding the lipase to the dough, any ingredient from which the dough is to be made, and/or any mixture of dough ingredients from which the dough is to be made. In other words, the lipase may be added in any step of the dough preparation and may be added in one, two, or more steps.

The term "effective amount" is defined herein as an amount of the lipase that is sufficient for providing a measurable effect on at least one property of interest of the dough and/or baked product.

The term "improved property" is defined herein as any property of a dough and/or a product obtained from the dough, particularly a baked product, which is improved by the action of the lipase relative to a dough or product in which a lipase is not incorporated. The improved property may include, but is not limited to, increased strength of the dough, increased elasticity of the dough, increased stability of the dough, reduced stickiness of the dough, improved extensibility of the dough, improved machinability of the dough, increased volume of the baked product, improved crumb structure of the baked product, improved softness of the baked product, improved flavor of the baked product, and/or improved antistaling of the baked product.

The use of the lipase may result in an increased strength, stability, and/or reduced stickiness of the dough, resulting in improved machinability, as well as in an increased volume and improved crumb structure and softness of the baked product. The effect on the dough may be particularly advantageous when a poor quality flour is used. Improved machinability is of particular importance in connection with dough that is to be processed industrially.

The improved property may be determined by comparison of a dough and/or a baked product prepared with and without addition of a lipase in accordance with the methods of the present invention. Techniques which can be used to determine improvements achieved by use of the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyzer (e.g., TAXT2) as known in the art.

The term "improved extensibility of the dough" is defined herein as the property of a dough that can be subjected to increased strain or stretching without rupture.

The term "improved machinability of the dough" is defined herein as the property of a dough that is generally less sticky and/or more firm and/or more elastic.

The term "increased volume of the baked product" is measured as the specific volume of a given loaf of bread (volume/weight) determined typically by the traditional rape seed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved antistaling of the baked product" is defined herein as the properties of a baked product that have a reduced rate of deterioration of quality parameters, e.g., softness and/or elasticity, during storage.

In a preferred embodiment, the one or more lipases improve one or more properties of the dough or the baked product obtained from the dough. In another preferred embodiment, the one or more lipases improve one or more properties of the dough and the baked product obtained from the dough.

In a preferred embodiment, the improved property is increased strength of the dough. In another preferred embodiment, the improved property is increased elasticity of the dough. In another preferred embodiment, the improved property is increased stability of the dough. In another preferred embodiment, the improved property is reduced stickiness of the dough. In another preferred embodiment, the improved property is improved extensibility of the dough. In another preferred embodiment, the improved property is improved machinability of the dough. In another preferred embodiment, the improved property is increased volume of the baked product. In another preferred embodiment, the improved property is improved crumb structure of the baked product. In another preferred embodiment, the improved property is improved softness of the baked product. In another preferred embodiment, the improved property is improved flavor of the baked product. In another preferred embodiment, the improved property is improved antistaling of the baked product.

The term "dough" is defined herein as a mixture of flour and other ingredients firm enough to knead or roll. The dough may be fresh, frozen, pre-bared, or pre-baked. The preparation of frozen dough is described by Kulp and Lorenz in *Frozen and Refrigerated Doughs and Batters.*

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

When the lipase is added to dough intended for use in the preparation of baked products, it may exert a useful modification of lipids present in the dough or dough constituents so as to soften the dough. The lipase is used in an amount sufficient to provide the desired effect, i.e., the improved properties in question. Thus, the dosage of the lipase to be used in the methods of the present invention should be adapted to the nature and composition of the dough in question.

The term "composition" is defined herein as a dough-improving and/or baked product-improving composition which, in addition to the lipase, comprise one or more additional substances conventionally used in baking. The additional substance(s) may be other enzymes or chemical additives known in the art to be useful in dough preparation and/or baking.

The bread-improving and/or dough improving composition of the invention is generally included in the dough in an amount corresponding to 0.01–5%, in particular 0.1–3%. The lipase(s) is typically added in an amount corresponding to 0.01–100 mg enzyme protein per kg of flour, preferably 0.1–25 mg enzyme protein per kg of flour, more preferably 0.1–10 mg enzyme protein per kg of flour, and most preferably 0.5–5 mg enzyme protein per kg of flour.

In terms of enzyme activity, the appropriate dosage of the lipase for exerting a desirable improvement of dough and/or baked products may be determined on the basis of methods known in the art.

The lipase and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme. Granulates and agglomerated powders may be prepared by conventional methods, e.g., by spraying the lipase onto a carrier in a fluid-bed granulator. The carrier may consist of particulate cores having a suitable particle size. The carrier may be soluble or insoluble, e.g., a salt (such as NaCl or sodium sulfate), sugar (such as sucrose or lactose), sugar alcohol (such as sorbitol), starch, rice, corn grits, or soy. The lipase and/or additional enzymes may be contained in slow-release formulations. Methods for preparing slow-release formulations are well known in the art. Liquid enzyme preparations may, for instance, be stabilized by adding nutritionally acceptable stabilizers such as a sugar, sugar alcohol, or another polyol, and/or lactic acid or another organic acid according to established methods.

For inclusion in pre-mixes or flour it is advantageous that the lipase is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, another lipase, phospholipase (useful for the modification of lipids present in the dough or dough constituents so as to soften the dough and improve gas retention in the dough), cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an aldose oxidase, glucose oxidase, pyranose oxidase, lipoxygenase, or L-amino acid oxidase (useful in improving dough consistency).

The xylanase is preferably of microbial origin, e.g., derived from a bacterium or fungus, such as a strain of Aspergillus, in particular of *Aspergillus aculeatus, Aspergillus niger* (cf. WO 91/19782), *Aspergillus awamori* (WO 91/18977), or *Aspergillus tubigensis* (WO 92/01793), from a strain of Trichoderma, e.g., *Trichoderma reesei*, or from a strain of Humicola, e.g.,*Humicola insolens* (WO 92/117573, the contents of which is hereby incorporated by reference).

Commercially available amylases useful in the present invention are NOVAMYL™ (a *Bacillus stearothermophilus* maltogenic amylase, available from Novo Nordisk A/S, Denmark), FUNGAMYL® (an *Aspergillus oryzae* alpha-amylase, available from Novo Nordisk A/S, Denmark), and BAN™ (a *Bacillus lichenifomis* alpha-amylase, available from Novo Nordisk A/S, Denmark). A commercially available amyloglucosidase useful in the present invention is AMG™ (an *Aspergillus niger* amyloglucosidase, available from Novo Nordisk A/S, Denmark). Other useful commercially available amylase products include GRINDAMYL™ A 1000 or A 5000 (available from Grindsted Products, Denmark) and AMYLASE H or AMYLASE P (available from Gist-Brocades, The Netherlands). A commercially available glucose oxidase useful in the present invention is GLUZYME™ (an *Aspergillus niger* glucose oxidase, available from Novo Nordisk A/S, Denmark). Commercially available proteases useful in the present invention are NEUTRASE™ (a *Bacillus amyloliquefaciens* endoprotease, available from Novo Nordisk A/S, Denmark) and GLUTENASE™ (available from Novo Nordisk A/S, Denmark). Commercially available pentosanase useful in the present invention are PENTOPAN™ (a *Humicola insolens* pentosanase, available from Novo Nordisk A/S, Denmark) and PENTOPAN™ MONO (a *Thermomyces lanuginosus* pentosanase, available from Novo Nordisk A/S, Denmark). A commercially available lipase useful in the present invention is NOVOZYM® 677 BG (a *Thermomyces lanuginosus* lipase, available from Novo Nordisk A/S, Denmark).

When one or more additional enzyme activities are to be added in accordance with the methods of the present invention, these activities may be added separately or together with the lipase(s), optionally as constituent(s) of the bread-improving and/or dough-improving composition. The other enzyme activities may be any of the enzymes described above and may be dosed in accordance with established baking practices.

In addition to the above-mentioned additional enzymes, the lipase may contain varying minor amounts of other enzymatic activities inherently produced by the producer organism in question.

In addition, or as an alternative, to additional enzyme components, a conventionally used baking agent(s) may also be incorporated into the dough. The baking agent may include proteins, such as milk powder (to provide crust colour), gluten (to improve the gas retention power of weak flours), and soy (to provide additional nutrients and improve water binding); eggs such (either whole eggs, egg yolks or egg whites); fat such as granulated fat or shortening (to soften the dough and improve the texture of the bread); emulsifier (to improve dough extensibility and, to some extent, the consistency of the resulting bread); oxidant, e.g., ascorbic acid, potassium bromate, potassium iodate, azodicarbon amide (ADA) or ammonium persulfate (to strengthen the gluten structure); amino acid, e.g., L-cysteine (to improve mixing properties); sugar; salt, e.g., sodium chloride, calcium acetate, sodium sulfate or calcium sulphate (to make the dough firmer); flour: and starch. Such components may also be added to the dough in accordance with the methods of the present invention.

Examples of suitable emulsifiers are mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, phospholipids, and lecithin.

The dough and/or baked product prepared by a method of the present invention may be based on wheat meal or flour, optionally in combination with other types of meal or flour such as corn meal, corn flour, rye meal, rye flour, oat meal, oat flour, soy meal, soy flour, sorghum meal, sorghum flour, potato meal, or potato flour.

The handling of the dough and/or baking may be performed in any suitable manner for the dough and/or baked product in question, typically including the steps of kneading the dough, subjecting the dough to one or more proofing treatments, and baking the product under suitable conditions, ie., at a suitable temperature and for a sufficient period of time. For instance, the dough may be prepared by using a normal straight dough process, a sour dough process, an overnight dough method, a low-temperature and long-time fermentation method, a frozen dough method, the Chorleywood Bread process, or the Sponge and Dough process.

From the above disclosure it will be apparent that the dough of the invention is generally a leavened dough or a dough to be subjected to leavening. The dough may be leavened in various ways such as by adding sodium bicarbonate or the like, or by adding a leaven (fermenting dough), but it is preferable that the dough be leavened by adding a suitable yeast culture, such as a culture of *Saccharomyces cerevisiae* (baker's yeast). Any of the commercially available *Saccharomyces cerevisiae* strains may be employed.

The present invention also relates to the use of a lipase for the preparation of pasta dough, preferably prepared from durum flour or a flour of comparable quality. The dough may be prepared by use of conventional techniques and the lipase(s) used in a similar dosage as that described above. The lipase(s) may be any of the types described above. When used in the preparation of pasta, the lipase(s) results in a strengthening of the gluten structure, a reduction in the dough stickiness, and increased dough strength.

The present invention also relates to methods for preparing a baked product, comprising baking a dough obtained by a method of the present invention to produce a baked product. The baking of the dough to produce a baked product may be performed using methods well known in the art.

The present invention also relates to compositions comprising an effective amount of one or more lipases, and a carrier and/or a baking ingredient. The compositions may further comprise a substrate for the lipase, one or more additional enzymes, one or more conventionally used baking agents, an enzyme which acts on a substance endogenous to the flour to produce a substrate for the lipase of interest, and/or a substance and the enzyme which acts on the substance to produce a substrate for the lipase.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a lipase. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing a lipase or a bread-improving and/or dough-improving composition of the invention comprising a lipase with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise the lipase. The baking additive preferably has a narrow particle size distribution with more than 95% (by weight) of the particles in the range from 25 to 500 $\mu$m.

The present invention is further described by the following examples that should not be construed as limiting the scope of the invention.

EXAMPLES

Materials and Methods

Sponge Dough

A liquid sponge is prepared by mixing 34.8 parts of water, 60 parts of flour and 1.5 parts of instant yeast, and fermenting for 3 hours at 24° C. A dough is then prepared by mixing the liquid sponge with 22.93 parts of water, 40 parts of flour, 0.5 part of instant yeast, 11.26 parts of 42 high-fructose corn syrup, 0.25 part of calcium propionate, 2 parts of oil and 2 parts of salt, 50 ppm of ascorbic acid 50 parts of wheat flour, 0.5 part of SSL (sodium stearoyl-2-lactylate), 2 parts of salt, 6 parts of sugar and water and ascorbic acid as required.

European Straight Dough Procedure

A dough is prepared by mixing 100 parts (by weight) of wheat flour, 4 parts of yeast, 1.5 parts of salt and 1.5 parts of sugar with water and ascorbic acid as required.

Loaf Specific Volume

The mean value of the volumes of 4 loaves are measured using the traditional rape seed method. The specific volume is calculated as volume ml per g bread. The specific volume of the control (without enzyme) is defined as 100. The relative specific volume index is the percentage of the specific volume of 4 loaves per the specific volume of 4 control loaves.

Firmness

The crumb firmness was measured using a texture analyzer TA-XT2 from Stable Micro Systems. Texture was measured according to a modified ACCA method (American Cereal Chemists' Association).

Shape Factor (Previously: Ascorbic Acid Factor)

The shape factor is taken as the ratio between the height and diameter of rolls after baking (average of 10 rolls).

Dough Stickiness

Stickiness is a measure of the degree to which a dough adheres to one's hands or other surfaces. It is evaluated by making a 3 cm deep cut in the middle of a dough and having a test panel feeling the cut. The results are expressed on a scale from 0 (less soft) to 10 (more soft) with the control (dough without enzyme addition) taken as 5.

Dough Softness

Softness is a measure of the degree to which, or ease with which, a dough will compress or resist compression. A sensory evaluation is done by a test panel feeling and squeezing the dough. The results are expressed on a scale from 0 (little stickiness) to 10 (very sticky) with the control (dough without enzyme addition) taken as 5.

Dough Extensibility

Extensibility is a measure of the degree by which a dough tends to recover its original shape after release from a deforming force. A sensory evaluation is done by a test panel pulling a piece of kneaded dough (about 30 g) and judging the suppleness and springiness. The results are expressed on a scale from 0 (high/long extensibility) to 10 (low/short extensibility) with the control (dough without enzyme addition) taken as 5.

Dough Elasticity

Elasticity is a measure of the degree to which a dough can be stretched without tearing. It is evaluated by rolling a piece of dough (about 30 g) to a size of about 10 cm, and having a test panel carefully pulling at opposite ends to judge the resistance and elasticity. The results are expressed on a scale from 0 (low/weak elasticity) to 10 (high/strong elasticity) with the control (dough without enzyme addition) taken as 5.

Gluten Strengthening

The strengthening effect of a given dough conditioner on wheat flour dough or gluten dough may be measured by dynamic rheological measurements. These measurements are able to show the strength of a dough under oscillation. Both wheat flour dough and gluten dough are viscoelastic materials. In oscillatory measurements, the viscoelastic properties of a wheat dough and a gluten dough can be divided into two components, the dynamic shear storage modulus G' and the dynamic shear loss modulus G". The ratio of the loss and the storage moduli is numerically equal to the tangent of the viscoelastic phase angle δ(Delta). An increase in the storage modulus G' and a decrease in the phase angle δ indicate a stronger and more elastic dough.

Strains

*Fusarum venenatum* WTY700 3.8d, a spore-purified tri5-minus, dps1-minus strain, was used as the recipient strain for transformation experiments. *Fusarium venenatum* WTY700 3.8d is a morphological mutant of *Fusarium venenatum* strain ATCC 20334 (Wiebe et al., 1991, *Mycol. Research* 95:1284–1288),

Example 1

Fermentation and Mycelial Tissue Preparation

*Fusarium venenatum* WTY700 3.8d was grown in a two-liter lab-scale fermentor using a fed-batch fermentation scheme with NUTRIOSE™ (Roquette Freres, S.A., Beinheim, France) as the carbon source and yeast extract. Ammonium phosphate was provided in the feed. The fermentation was maintained at pH 6–6.5 and 30° C. with positive dissolved oxygen.

Mycelial samples were harvested at 2, 4, 6, and 8 days post-inoculum and quick-frozen in liquid nitrogen. The samples were stored at −80° C. until they were disrupted for RNA extraction.

Example 2 cDNA Library Construction

Total cellular RNA was extracted from the mycelial samples described in Example 1 according to the method of Timberlake and Barnard (1981, *Cell* 26: 29–37), and the RNA samples were analyzed by Northern hybridization after blotting from 1% formaldehyde-agarose gels (Davis et al., 1986, *Basic Methods in Molecular Biology*, Elsevier Science Publishing Co., Inc., New York). Polyadenylated mRNA fractions were isolated from total RNA with an mRNA Separator Kit™ (Clontech Laboratories, Inc., Palo Alto, Calif.) according to the manufacturer's instructions. Double-stranded cDNA was synthesized using approximately 5 µg of poly(A)+mRNA according to the method of Gubler and Hoffman (1983, *Gene* 25: 263–269) except a NotI-(dT)18 primer (Pharmacia Biotech, Inc., Piscataway, N.J.) was used to initiate first strand synthesis. The cDNA was treated with mung bean nuclease (Boehringer Mannheim Corporation, Indianapolis, Ind.) and the ends were made blunt with T4 DNA polymerase (New England Biolabs, Beverly, Mass.).

The cDNA was digested with NotI, size selected by agarose gel electrophoresis (ca. 0.7–4.5 kb), and ligated with pZErO-2.1 (Invitrogen Corporation, Carlsbad, Calif.) which had been cleaved with NotI plus EcoRV and dephosphorylated with calf-intestine alkaline phosphatase (Boehringer Mannheim Corporation, Indianapolis, Ind.). The ligation mixture was used to transform competent *E. coli* TOP10 cells (Invitrogen Corporation, Carlsbad, Calif.). Transformants were selected on 2YT agar plates (Miller, 1992, *A Short Course in Bacterial Genetics. A Laboratory Manual and Handbook for Escherichia coli and Related Bacteria*,

Example 3

Template Preparation and Nucleotide Sequencing

From the cDNA library described in Example 2, 1192 transformant colonies were picked directly from the transformation plates into 96-well microtiter dishes which contained 200 μl of 2YT broth (Miller, 1992, supra) with 50 μg/ml kanamycin. The plates were incubated overnight at 37° C. without shaking. After incubation 100 μl of sterile 50% glycerol was added to each well. The transformants were replicated into secondary, deep-dish 96-well microculture plates (Advanced Genetic Technologies Corporation, Gaithersburg, Md.) containing 1 ml of Magnificent Broth™ (MacConnell Research, San Diego, Calif.) supplemented with 50 μg of kanamycin per ml in each well. The primary microtiter plates were stored frozen at −80° C. The secondary deep-dish plates were incubated at 37° C. overnight with vigorous agitation (300 rpm) on rotary shaker. To prevent spilling and cross-contamination, and to allow sufficient aeration, s each secondary culture plate was covered with a polypropylene pad (Advanced Genetic Technologies Corporation, Gaithersburg, Md.) and a plastic microtiter dish cover.

DNA was isolated from each well using the 96-well Miniprep Kit protocol of Advanced Genetic Technologies Corporation (Gaithersburg, Md.) as modified by Utterback et al. (1995, *Genome Sci. Technol.* 1: 1–8). Single-pass DNA sequencing (EST) was done with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, *Journal of Virology Methods* 38: 47–60) and the reverse lac sequencing primer.

Example 4

Analysis of DNA Sequence Data

Nucleotide sequence data were scrutinized for quality, and samples giving improper spacing or ambiguity levels exceeding 3% were discarded or re-run. Vector sequences and ambiguous base calls at the ends of the DNA sequences were trimmed with assistance of FACTURA™ software (Perkin-Elmer Applied Biosystems, Inc., Foster City, Calif. All sequences were compared to each other to determine multiplicity using AutoAssembler™ software (Perkin-Elmer Applied Biosystems, Inc., Foster City, Calif.). Lastly, all sequences were translated in three frames and searched against a non-redundant database (NRDB) using GeneAssist™ software (Perkin-Elmer Applied Biosystems, Inc., Foster City, Calif.) with a modified Smith-Waterman algorithm using the BLOSUM 62 matrix with a threshold score of 70. The NRDB was assembled from Genpept, Swiss-Prot, and PIR databases.

Example 5

Identification of Lipase 1 cDNA Clones

Putative lipase clones were identified by comparing the deduced amino acid sequence of the ESTs to protein sequences deposited in publicly available databases such as Swissprot, Genpept, and PIR using a modified Smith-Waterman search algorithm (Perkin-Elmer Applied Biosystems, Foster City, Calif.). Tentative identification was based on amino acid sequence similarity to numerous fungal lipases. One clone, *Fusarium venenatum* EST FA0726, was selected for nucleotide sequence analysis which revealed that the cDNA clone was truncated at its 5 prime end.

Example 6

Fusarium Venenatum Genomic DNA Extraction

*Fusarium venenatum* WTY700 was grown for 24 hours at 28° C. and 150 rpm in 25 ml of YEG medium composed per liter of 5 g of yeast extract and 20 g of glucose. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol:chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer. DNase-free ribonuclease A was added to a concentration of 100 μg/ml and the mixture was incubated at 37° C. for 30 minutes. Proteinase K (200 μg/ml) was then added and the mixture was incubated an additional hour at 37° C. Finally, the mixture was extracted twice with phenol:chloroform:isoamyl alcohol (25:24:1 v/v/v) before precipitating the DNA with sodium acetate and ethanol according to standard procedures. The DNA pellet was dried under vacuum, resuspended in TE buffer, and stored at 4° C.

Example 7

Genomic DNA Library Construction, Screening, and Isolation of Genomic Lipase 1 Clone Genomic libraries of *Fusarium venenatum* WTY700 were constructed in λZipLox according to the manufacturer's instructions (Life Technologies, Gaithersburg, Md.). *Fusarium venenatum* genomic DNA was partially digested with Tsp509I and size-fractionated on 1% agarose gels. DNA fragments migrating in the size range 3–7 kb were excised and eluted from the agarose gel slices using Prep-a-Gene reagents (BioRad, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *E. coli* Y1090ZL cells.

The cDNA from *Fusarium venenatum* clone FA0726 was excised from the vector plasmid by digestion with EcoRI and NotI yielding an approximately 900 bp fragment. The fragment was purified by gel electrophoresis, and radiolabeled with α[$^{32}$P] dCTP using a Prime-it Random Primer Labeling Kit (Stratagene, La Jolla, Calif.).

Approximately 40,000 plaques from the library were screened by plaque-hybridization (Davis et al., 1980, supra) with the radiolabeled probe fragment of the *Fusarium venenatum* lipase gene using high stringency conditions at 45° C. (high stringency=50% formamide, 5×SSPE, 0.3%

SDS, 200 μg/ml sheared and denatured salmon sperm DNA). Plaques, which gave hybridization signals, were purified once in *E. coli* DH10B cells, and the individual clones were subsequently excised from the λZipLox vector as pZL1-derivatives (D'Alessio et al., 1992, Focus® 14: 7). One plaque was identified that hybridized strongly to the *Fusarium venenatum* lipase gene probe, and was subsequently excised from the λZipLox vector as a pZL1-derivative (D'Alessio et al., 1992, supra). Plasmid DNA was isolated from the clone by passage through *E. coli* DH10B cells (Life Technologies, Gaithersburg, Md.) according to the manufacturer's instructions. This clone was designated *E. coli* DH10B -pFvLipase1.

Example 8

Characterization of the *Fusarium venenatum* Genomic Clone Encoding Lipase 1

DNA sequencing was performed on an Perkin-Elmer Biosystems Model 377 XL Automated DNA Sequencer using dye-terminator chemistry (Giesecke et al., 1992, *Journal of Virology Methods* 38: 47–60). Contig sequences were generated using a transposon insertion strategy (Primer Island Transposition Kit, Perkin-Elmer/Applied Biosystems, Inc., Foster City, Calif.). The 2.94 kb genomic fragment was sequenced to an average redundancy of 4.8.

Figure 1A:
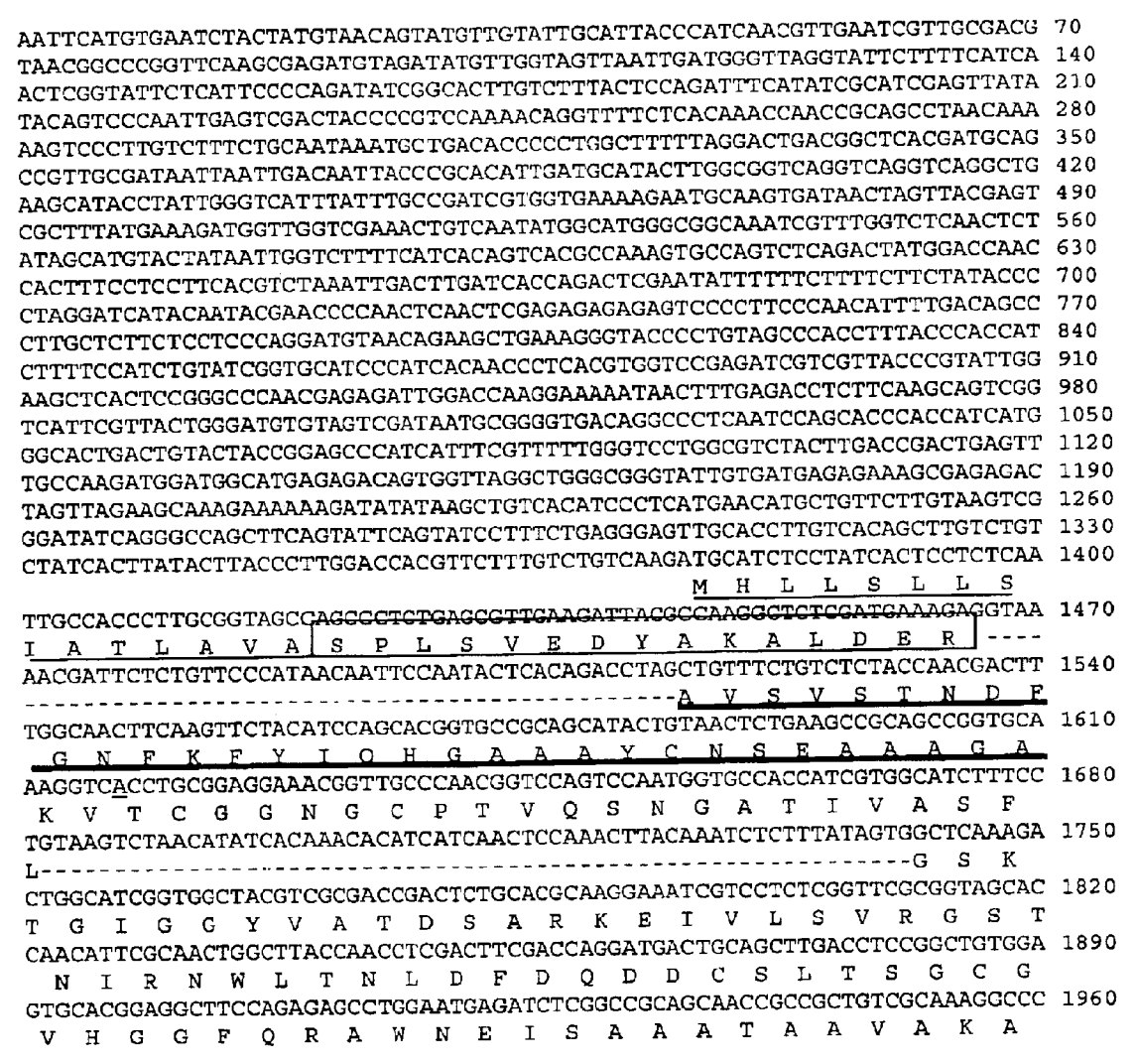

The nucleotide sequence and deduced amino acid sequence are shown in FIG. 1. The insert contains an open reading frame of 1.153 kb encoding a polypeptide of 350 amino acids. Using the SignalP software program (Nielsen et al., 1997, *Protein Engineering* 10: 1–6), a signal peptide of 15 residues was predicted. The predicted signal peptide is followed by a 15 residue propeptide ending with a concanical propeptide Glu/Arg cleavage site. N-terminal sequencing of the lipase 1 protein supports this propeptide cleavage site prediction. The open reading frame is interrupted by two introns of 49 bp and 58 bp. Thus, the mature *Fusarium venenatum* lipase comprises 319 amino acids and a predicted molecular weight of 33.6 kDa. There are 2 potential N-linked glycosylation sites (Asn-X-Ser/Thr) within *Fusarium venenatum* lipase 1.

A comparative alignment of lipase sequences using the Clustal W algorithm in the Megalign program of DNA-Star, showed that the deduced amino acid sequence of the *Fusarium venenatum* lipase 1 gene shares 81% identity to the deduced amino acid sequence of a *Fusarium oxysporum* phospholipase A (EP0869167).

Example 9

Construction of Plasmid PSheB1

The *Fusarium venenatum* expression vector pSheB1 (FIG. 2) was generated by modification of pDM181 (WO 98/20136). The modifications included (a) removal of two NcoI sites within the pDM181 sequence, and (b) restoration of the natural translation start of the *Fusarium oxysporum* trypsin promoter (reconstruction of an NcoI site at the ATG start codon).

Removal of two NcoI sites within the pDM181 sequence was accomplished using the QuikChange™ site-directed mutagenesis kit (Stratagene Cloning Systems, La Jolla, Calif.) according to the manufacturer's instruction with the following pairs of mutagenesis primers:

5'-dCAGTGAATTGGCCTCGATGGCCGCGGCCGC GAATT-3' plus (SEQ ID NO:3)

5'-dAATTCGCGGCCGCGGCCATCGAGGCCATTCA CTG-3' (SEQ ID NO:4)

5'-dCACAAGGAAAGACGATGGCTTTCACGGTGT CTG-3' plus (SEQ ID NO:5)

5'-dCAGACACCGTGAAAGCCATCGTCTTTCCTT CGTG-3' (SEQ ID NO:6)

Restoration of the natural translation start of the Fusarium oxysporum trypsin promoter was also accomplished using the Stratagene QuikChange™ site directed mutagenesis kit in conjunction with the following pair of mutagenesis primers:

5'-dCTATCTCTTCACCATGGTACCTTMTTAAATA CCTTGTTGGAAGCG-3' plus (SEQ ID NO:7)

5'-dCGCTTCCAACAAGGTATTTAATTAAGGTACC ATGGTGAGAGATAG-3' (SEQ ID NO:8)

All site-directed changes were confirmed by DNA sequence analysis of the appropriate vector regions.

Example 10

Construction of Expression Vector pEJG60

The lipase-expression vector, pEJG60 was constructed as follows. The lipase coding region was amplified from pFv-lipase1 using the following pair of primers: Primer 990658:

5'-CGTTCTTTGTCTGTCAGCATGCATCTCCTATCA CTCC-3' (SEQ ID NO:9) Primer 990661:

5'-CCAGAGTTTTTGTTATGGTTAATTAATATCGTT ACTGCGTAAATG-3' (SEQ ID NO:10)

The forward primer introduces a SphI site which contains the ATG, and the reverse primer introduces a PacI site after the stop codon.

The amplification reaction (100 μl) contained the following components: 0.5 μg of genomic clone pFvLipase1, 50 pmol of the forward primer, 50 pmol of the reverse primer, 10 mM dNTPs (dATP, dCTP, dGTP, and dTTP), 1× Pwo DNA polymerase buffer, and 2.5 units of Pwo DNA polymerase (Boehringer Mannheim, Indianapolis, Ind.). The reactions were incubated in a Perkin-Elmer Model 480 Thermal Cycler programmed for 1 cycles at 95° C. for 2 minutes; 10 cycles at 94° C. for 45 seconds, 55° C. for 45 seconds, and 72° C. for 2 minutes; 17 cycles at 94° C. for 45 seconds, 55° C. for 45 seconds, and 72° C. for 2 minutes with an extension of 20 seconds per cycle; 1 cycle at 72° C. for 10 minutes; and a soak cycle at 4° C. The reaction products were isolated on a 1% agarose gel where a 1.15 kb product band was excised from the gel and purified using Qiaquik Gel Extraction Kit (Qiagen, Chatsworth, Calif.) according to the manufacturer's instructions.

Figure 3:
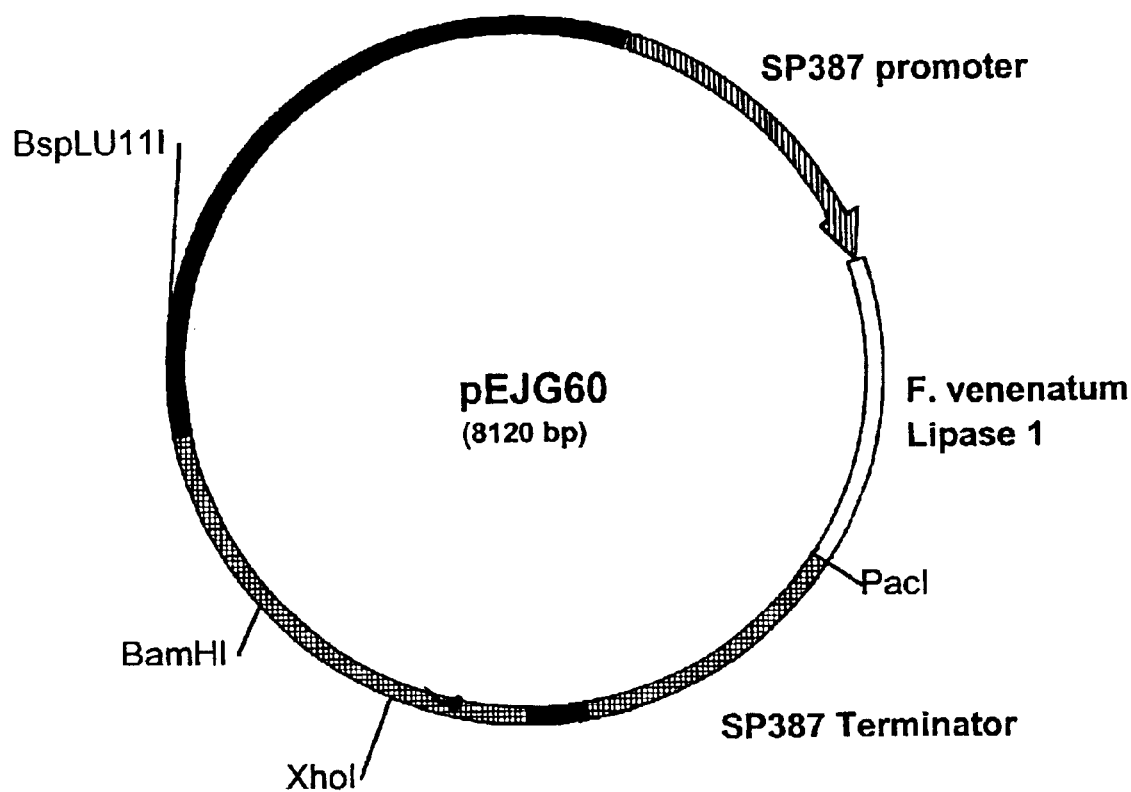
FIG. 3 show a restriction map of pEJG60.

The generated fragment was digested with ShpI, blunted with Klenow, digested with PacI, and purified by agarose gel electrophoresis and Qiaquik Gel Extraction Kit (Qiagen, Chatsworth, Calif.). The purified DNA segment was ligated into pSheB1 (FIG. 2) which was previously NcoI digested, treated with DNA polymerase I (Klenow fragment), and digested with PacI. The treatment of the NcoI-digested vector with Klenow fragment resulted in a filling in of the NcoI cohesive end, thereby making it blunt and compatible with the blunt site of the lipase DNA segment. The resulting expression plasmid was designated pEJG60 (FIG. 3). The PCR-amplified lipase gene segment was re-sequenced to verify the absence of any errors.

Example 11

Transformation of *Fusarium venenatum* and Analysis of *Fusarium venenatum* Transformants Spores of *Fusarium venenatum* WTY700 were generated by inoculating a flask containing 500 ml of RA sporulation medium with 10 plugs from a 1×Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4 \times 10^7$ spores of *Fusarium venenatum* WTY700 and incubating for 16 hours at 24° C. and 150 rpm. The culture was centrifuged for 7 minutes at 3500 rpm in a Sorvall RT 6000D (E. I. DuPont De Nemours and Co., Wilmington, Del. Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M s sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25 \times 10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* WTY700 were thawed on ice. Five μg of pEJG60 described in Example 10 and 5 μl of heparin (5 mg per ml of STC) was added to a 50 ml sterile polypropylene tube. One hundred μl of protoplasts was added, mixed gently, and incubated on ice for 30 minutes. One ml of SPTC was added and incubated 20 minutes at room temperature. After the addition of 25 ml of 40° C. COVE top agarose, the mixture was poured onto an empty 150 mm diameter plate and incubated overnight at room temperature. Then an additional 25 ml of 40° C. COVE top agarose containing 10 mg of BASTA™ per ml was poured on top of the plate and incubated at room temperature for up to 14 days. The active ingredient in the herbicide BASTA™ is phosphinothricin. BASTAT™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Twenty-four transformants were picked directly from the selection plates (COVE underlay with COVE-BASTA™ overlay) and inoculated into 125 ml shake flasks containing 25 ml of M400Da medium supplemented with 1 mM $CaCl_2$ and 100 μg/ml ampicillin (to prevent bacterial contamination) and incubated at 28° C., 200 rpm on a platform shaker for 7 days. The untransformed recipient strain was also included as a negative control.

Flasks were sampled at 5 and 7 days and assayed for lipase activity as described below. The samples were also submitted to SDS-PAGE using Novex gradient gels (Novex Experimental Technology, San Diego, Calif.).

Lipase activity was determined as follows: 100 μl of substrate (3.92 ml of 100 mM MOPS pH 7.5, 4 mM $CaCl_2$, 990 μl of DMSO, 80 μl of 1% AOS, and 20 μl of p-nitrophenyl butyrate) was added to 100 μl of diluted sample. The samples were diluted accordingly in 100 mM MOPS pH 7.5, 4 mM $CaCl_2$. The absorbance at 405 nm was monitored for 3 minutes at room temperature in a 96-well microtiter plate using a Molecular Devices Thermomax Microplate Reader.

The lipase assay results indicated that at both 5 and 7 days, most of the transformants produced lipase activity well above that of the untransformed control.

Shake flask culture broths from transformants #1 and #3, the two highest scorers in the lipase assay, were analyzed on a 16% tricine gel. A prominent polypeptide at a apparent molecular weight of 32–33 kD was observed at both time points and for each transformant harboring pEJG60.

Example 12

Preparation of Straight-dough Bread

Doughs were made using spiral mixers from 2 kg of Meneba flour (batch 941–2) according to the straight dough method (AACC Method 10–10B in Approved Methods of the American Association of Cereal Chemists, Ninth Edition, March 1995; AACC, St. Paul Minn., USA).

Lipase activity was determined using pH-stat titration and tributyrin as substrate at 30° C. and pH 7. One unit of lipase activity (1 LU) equals the amount of enzyme capable of releasing 1 μmol butyric acid/minute under standard conditions. 1 KLU=1000 LU. Enzymes were dosed according to the protocol below:

| Dough Enzyme | 1 | 2 | 3 | 4 | 5 | 6 | 7 | 8 |
|---|---|---|---|---|---|---|---|---|
| *F. venenatum* Lipase LU/kg flour | | | 10 | 20 | 40 | 80 | 100 | 150 |
| *F. oxysporum* Lipase LU/kg flour | | 1000 | | | | | | |
| Fungamyl FAU/kg flour | 10 | 10 | 10 | 10 | 10 | 10 | 10 | 10 |
| PentMono FXU/kg flour | 100 | 100 | 100 | 100 | 100 | 100 | 100 | 100 |
| DATEM % | 0.4 | | | | | | | |

Example 13

Dough and Bread Evaluation and Dough Stability Measurements

Each dough described in Example 11 was split into 15 rolls for 45 minute fermentation; 15 rolls for 70 minute fermentation. Two pan breads were evaluated for of the breads crumb structure; and 2 pan breads were evaluated for texture analysis.

Firmness, elasticity of the doughs, and crumb structure, texture of the breads, shape factor and volume of the rolls were measured using the methods described earlier. Bread was measured 2 and 24 hours after baking.

Figure 4:
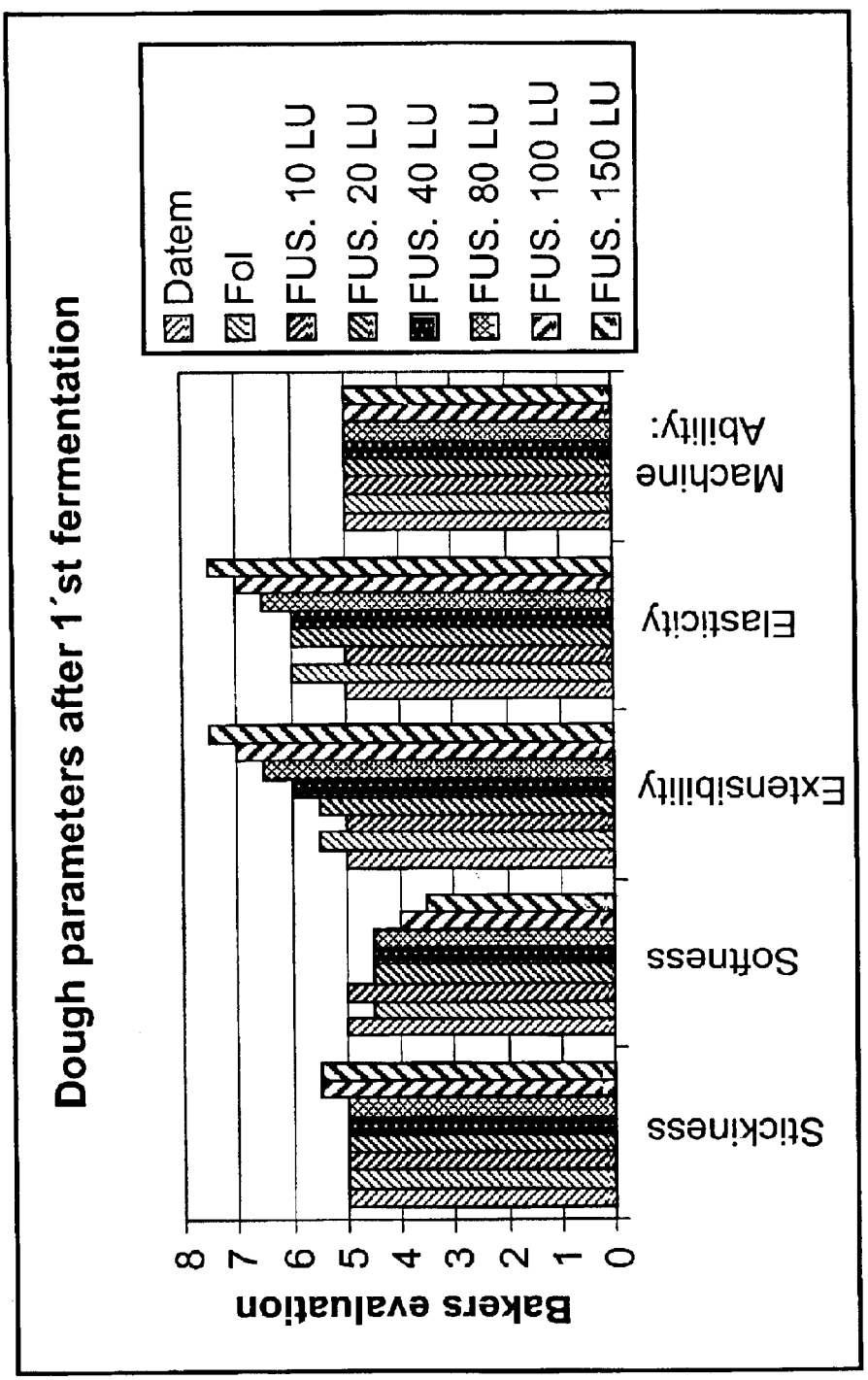
FIG. 4 shows the scores from a baker's evaluation of dough parameters after first fermentation.
Figure 5:
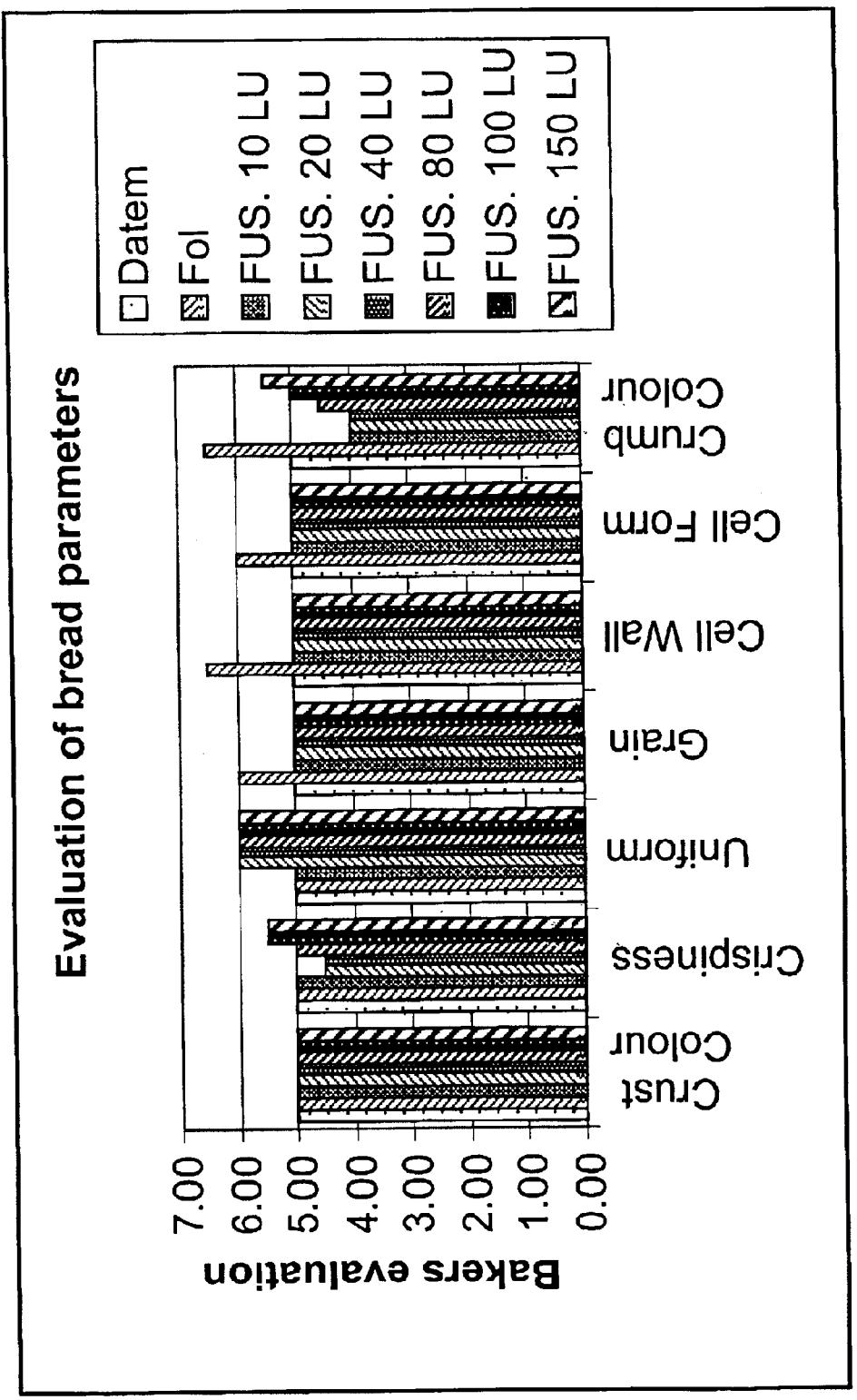
FIG. 5 shows the scores from a bakers evaluation of bread parameters.

Dough parameters are shown in FIG. 4 and bread parameters in FIG. 5.

The results of Dough 5 showed that the effect of the *Fusarium venenatum* lipase dosed at 40 LU/kg flour was similar to that of the *Fusarium oxysporum* lipase dosed at 1000 LU/kg flour. Increased dosages of the *Fusarium venenatum* lipase resulted in softer, more sticky dough which had a lower extensibility and higher elasticity. At a dosage of 150 LU/kg flour, the *Fusarium venenatum* lipase yielded a dough which broke apart easily when stretched, similar to undermixed doughs.

The effect of the *Fusarium venenatum* lipase on dough parameters was dosage dependent. The effect of the *Fusarium venenatum* lipase on bread was not significant. Generally *Fusarium oxysporum* lipase yielded a less uniform crumb, a finer grain with thinner cell walls and more elongated shape, and a whiter crumb colour compared to bread made from dough treated with the *Fusarium venenatum* lipase.

The effect of the lipases on stability is shown in Tables 1 and 2 at 45 minutes and 70 minutes, respectively. After normal fermentation time, addition of the *Fusarium venenatum* lipase yielded a very good stability factor when dosed at and above 80 LU/kg flour. At dosages of 100 and 150 LU of the *Fusarium venenatum* lipase per kg flour, the volume of the bread matched that of DATEM-treated (di-acetylated-tartaric acid-esters of mono-and diglycerides of fatty acids) bread, but was slightly smaller than that of the bread treated with the *Fusarium oxysporum* lipase. The best shape-factors were obtained with the high dosages of the *Fusarium venenatum* lipase.

TABLE 1

| | Bread | |
|---|---|---|
| Lipolytic enzyme added | Sp. Vol. (ml/g) 45 min | Shape factor 45 min |
| Datem | 6.89 | 0.672 |
| *F. oxysporum* (200LU) | 7.18 | 0.696 |
| *F. venenatum* (10LU) | 6.34 | 0.663 |
| *F. venenatum* (20LU) | 6.64 | 0.681 |
| *F. venenatum* (40LU) | 6.45 | 0.653 |
| *F. venenatum* (80LU) | 6.51 | 0.687 |
| *F. venenatum* (100LU) | 6.75 | 0.716 |
| *F. venenatum* (150LU) | 6.85 | 0.700 |

TABLE 2

| | Bread | |
|---|---|---|
| Lipolytic enzyme added | Sp. Vol. (ml/g) 70 min | Shape factor 70 min |
| Datem | 8.11 | 0.652 |
| *F. oxysporum* (200LU) | 7.96 | 0.682 |
| *F. venenatum* (10LU) | 6.76 | 0.648 |
| *F. venenatum* (20LU) | 6.79 | 0.655 |
| *F. venenatum* (40LU) | 6.94 | 0.651 |
| *F. venenatum* (80LU) | 7.54 | 0.672 |
| *F. venenatum* (100LU) | 7.69 | 0.678 |
| *F. venenatum* (150LU) | 7.78 | 0.680 |

After extended fermentation time, 80–150 LU/kg flour of the *Fusarium venenatum* lipase yielded a better shape-factor than DATEM, and 150 LU/kg flour of the *Fusarium venenatum* lipase performed as well as the *Fusarium oxysporum* lipase. A larger volume was achieved with increased dosage of the *Fusarium venenatum* lipase, where at 150 LU of the lipase per kg of flour, the volume increase nearly matched the volume increase with the *Fusarium oxysporum* lipase and DATEM.

The Fusarum oxysporum lipase overall performed best after normal and extended fermentation time with regard to bread volume and shape-factor. DATEM matched the *Fusarium oxysporum* lipase on volume after extended fermentation time. When dosed at 100 and 150 LU/kg flour, the *Fusarium venenatum* lipase yielded a better shape-factor, but lower volume after normal fermentation time than the *Fusarium oxysporum* lipase. After an extended fermentation time, 100 and 150 LU/kg flour of *Fusarium venenatum* lipase performed as well as to the *Fusarium oxysporum* lipase.

Figure 6:
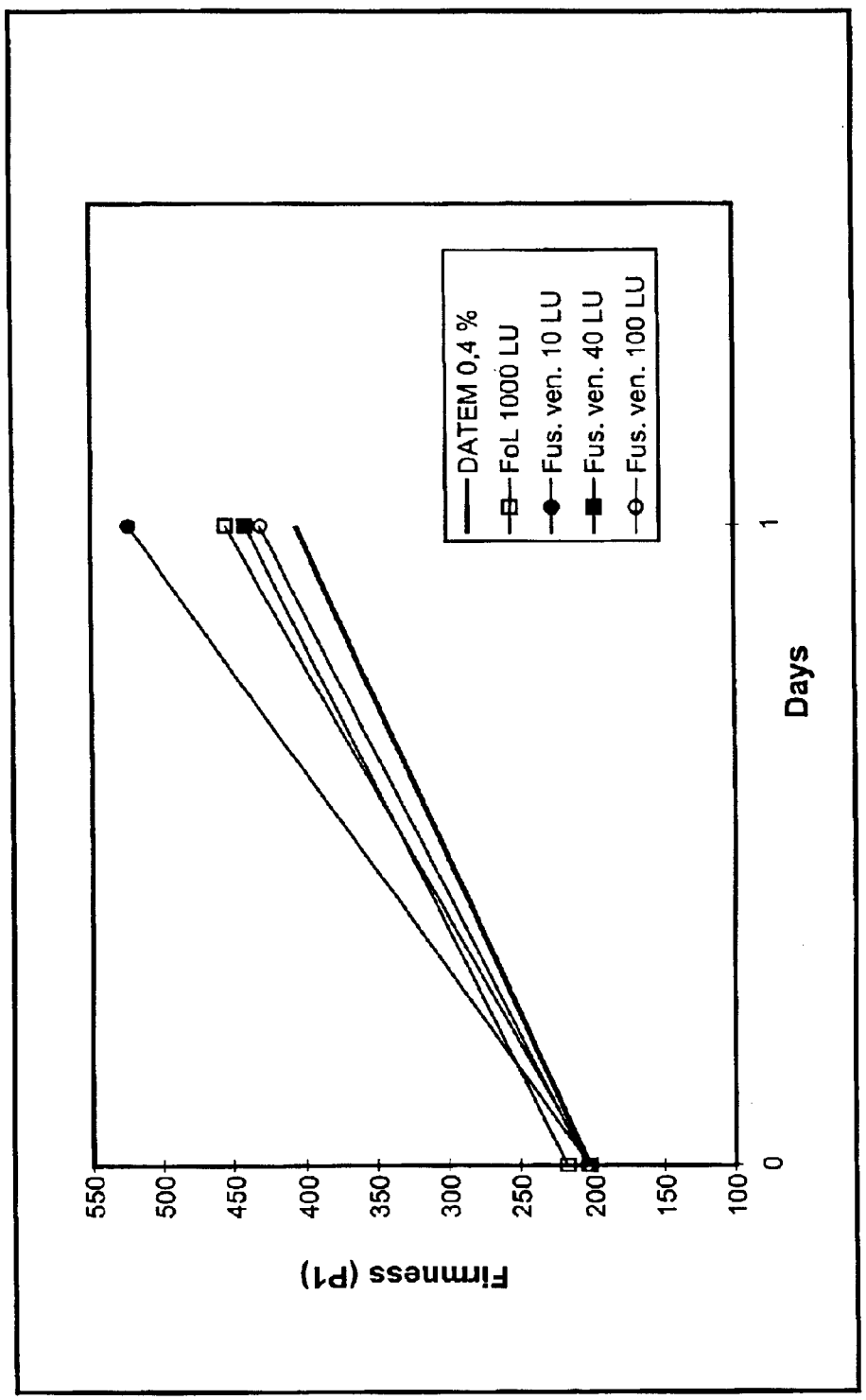
FIG. 6 shows the firmness measured during the first 24 hours after baking.
Figure 7:
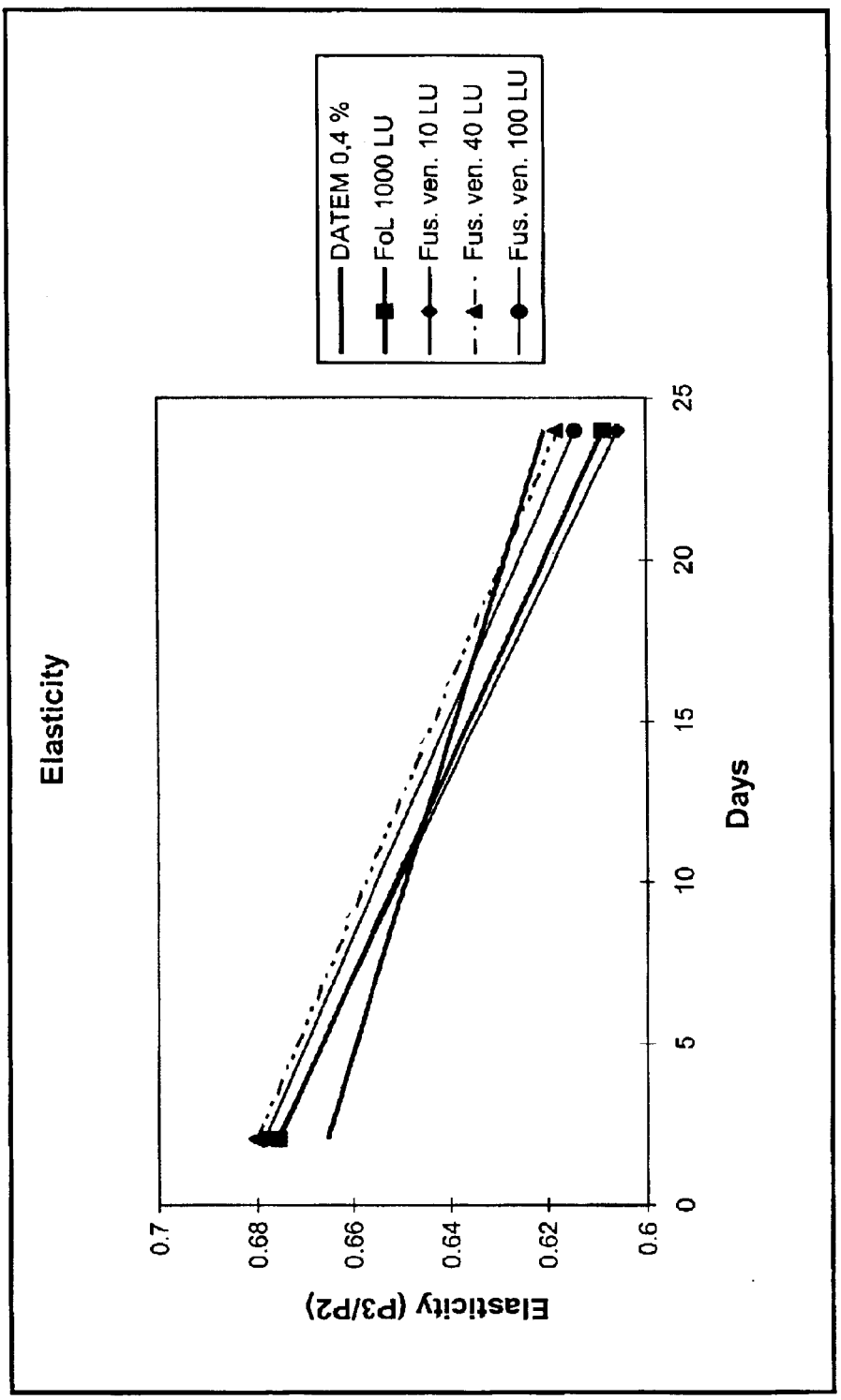
FIG. 7 shows the elasticity measured during the first 24 hours after baking.

Firmness and elasticity during the first 24 hours after baking are shown in FIGS. 6 and 7. The *Fusarium venenatum* lipase performed similarly to the *Fusarium oxysporum* lipase on initial softness and elasticity.

The overall optimal dosage of the *Fusarium venenatum* lipase was between 80–150 LU/kg flour, which corresponded to approximately 0.4–0.7 mg enzyme/kg flour. The optimal performance of *Fusarium venenatum* lipase appeared to be very close to that of the *Fusarium oxysporum* lipase at the optimal dosage of 1000 LU per kg flour corresponding to 0,33 mg enzyme/kg flour.

DEPOSIT OF BIOLOGICAL MATERIAL

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| *E. coli* pEJG60 | NRRL B-30333 | Aug. 22, 2000 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A pre-mix for a dough comprising a baking agent and an effective amount of a lipase selected from the group consisting of:
   (a) a lipase having an amino acid sequence which has at least 85% identity with amino acids 31 to 349 of SEQ ID NO:2;
   (b) a lipase encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, or (iii) a complementary strand of (i) or (ii); and
   (c) a fragment of (a) or (b), which has lipase activity.

2. The pre-mix of claim 1, wherein the lipase has an amino acid sequence which has at least 85% identity with amino acids 31 to 349 of SEQ ID NO:2.

3. The pre-mix of claim 2, wherein the lipase has an amino acid sequence which has at least 90% identity with amino acids 31 to 349 of SEQ ID NO:2.

4. The pre-mix of claim 3, wherein the lipase has an amino acid sequence which has at least 95% identity with amino acids 31 to 349 of SEQ ID NO:2.

5. The pre-mix of claim 1, wherein the lipase comprises the amino acid sequence of SEQ ID NO:2.

6. The pre-mix of claim 1, wherein the lipase consists of the amino acid sequence of SEQ ID NO:2 or a fragment thereof which has lipase activity.

7. The pre-mix of claim 6, wherein the lipase consists of the amino acid sequence of SEQ ID NO:2.

8. The pre-mix of claim 7, wherein the lipase consists of amino acids 31 to 349 of SEQ ID NO:2.

9. The pre-mix of claim 1, wherein the lipase is encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, or (iii) a complementary strand of (i) or (ii).

10. The pre-mix of claim 1, wherein the lipase is encoded by the nucleic acid sequence contained in plasmid pEJG60 which is contained in E. coli NRRL B30333.

11. A baking additive in the form of a granulate or agglomerated powder, comprising an effective amount of a lipase selected from the group consisting of.
   (a) a lipase having an amino acid sequence which has at least 85% identity with amino acids 31 to 349 of SEQ ID NO:2;
   (b) a lipase encoded by a nucleic acid sequence which hybridizes under high stringency conditions with (i) nucleoides 1525 to 2530 of SEQ ID NO:1, (ii) the cDNA sequence contained in nucleotides 1525 to 2530 of SEQ ID NO:1, or (iii) a complementary strand of (i) or (ii); and
   (c) a fragment of (a) or (b), which has lipase activity.

12. The baking additive of claim 11, wherein the lipase has an amino acid sequence which has at least 85% identity with amino acids 31 to 349 of SEQ ID NO:2.

13. The baking additive of claim 12, wherein the lipase has an amino acid sequence which has at least 90% identity with amino acids 31 to 349 of SEQ ID NO:2.

14. The baking additive of claim 13, wherein the lipase has an amino acid sequence which has at least 95% identity with amino acids 31 to 349 of SEQ ID NO:2.

15. The baking additive of claim 11, wherein the lipase comprises the amino acid sequence of SEQ ID NO:2.

16. The baking additive of claim 11, wherein the lipase consists of the amino acid sequence of SEQ ID NO:2 or a fragment thereof which has lipase activity.

17. The baking additive of claim 16, wherein the lipase consists of the amino acid sequence of SEQ ID NO:2.

18. The baking additive of claim 17, wherein the lipase consists of amino acids 31 to 349 of SEQ ID NO:2.

19. The baking additive of claim 11, wherein the lipase is encoded by a nucleic acid sequence which hybridizes under high stringency conditions with (i) nucleotides 1525 to 2530 of SEQ ID NO:1, (ii) the cDNA sequence contained in nucleotides 1525 to 2530 of SEQ ID NO:1, or (ii) a complementary strand of (i) or (ii).

20. The baking additive of claim 11, wherein the lipase is encoded by the nucleic acid sequence contained in plasmid pEJG60 which is contained in E. coli NRRL B30333.

* * * * *